United States Patent [19]
Stivender et al.

[11] 4,062,518
[45] Dec. 13, 1977

[54] X-RAY SHIELDING DEVICE

[75] Inventors: Paul M. Stivender, Waukesha; George R. Lang; Raymond C. Mentink, both of New Berlin, all of Wis.

[73] Assignee: General Electric Company, Schenectady, N.Y.

[21] Appl. No.: 740,569

[22] Filed: Nov. 10, 1976

[51] Int. Cl.² ............................................ G21C 11/00
[52] U.S. Cl. .................................. 250/519; 250/515; 250/452
[58] Field of Search ...................... 250/519, 515, 452

[56] References Cited
U.S. PATENT DOCUMENTS

| | | | |
|---|---|---|---|
| 3,030,508 | 4/1962 | Mort et al. | 250/515 |
| 3,286,094 | 11/1966 | Pretto | 250/519 |
| 3,967,129 | 6/1976 | Winkler | 250/519 |
| 3,984,696 | 10/1976 | Collica | 250/519 |

Primary Examiner—Harold A. Dixon
Attorney, Agent, or Firm—Ralph G. Hohenfeldt

[57] ABSTRACT

On a diagnostic x-ray table, a first group of x-ray shielding panels are supported for rotation on a carrier and another group of panels are supported on a lever that is pivotally connected to the carrier. The lever may be aligned with the carrier to present the combined width of all panels across the front of a combination spot film and fluoroscopic device. Means responsive to pivoting the lever along the side of the apparatus rotate the first group of panels to substantial parallelism with second group to present the panels along the side of the apparatus when the spot film and fluoroscope device is angulated to put the patient being examined in an erect posture.

13 Claims, 13 Drawing Figures

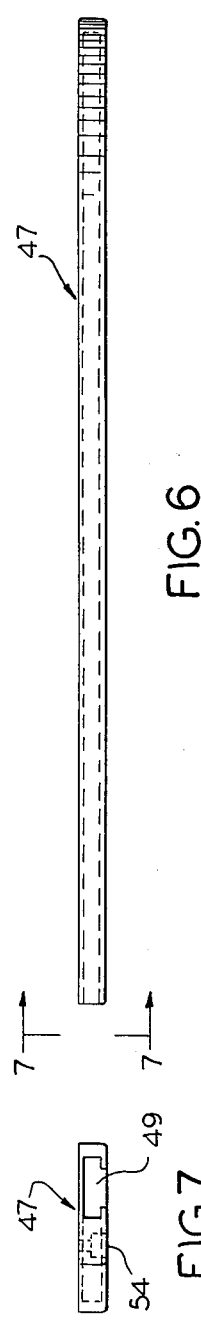
FIG.6
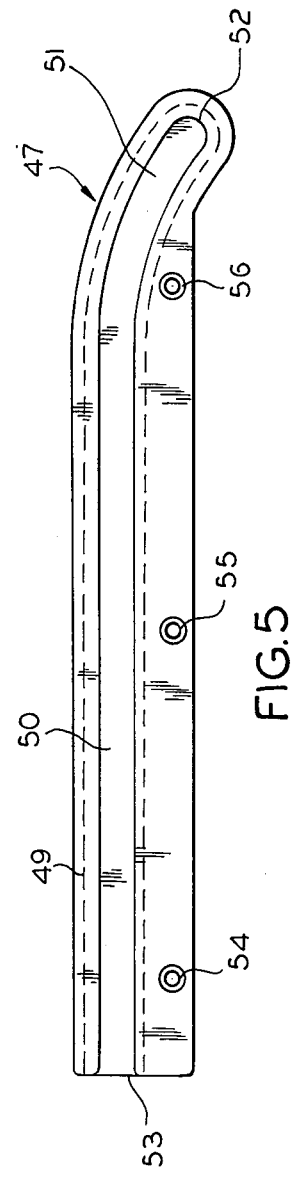
FIG.5
FIG.7
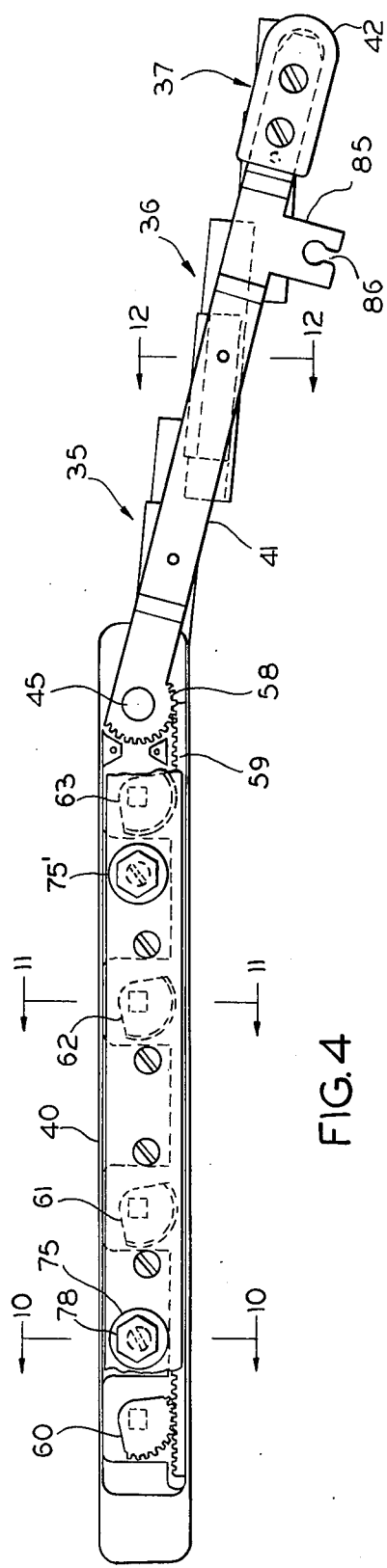
FIG.4

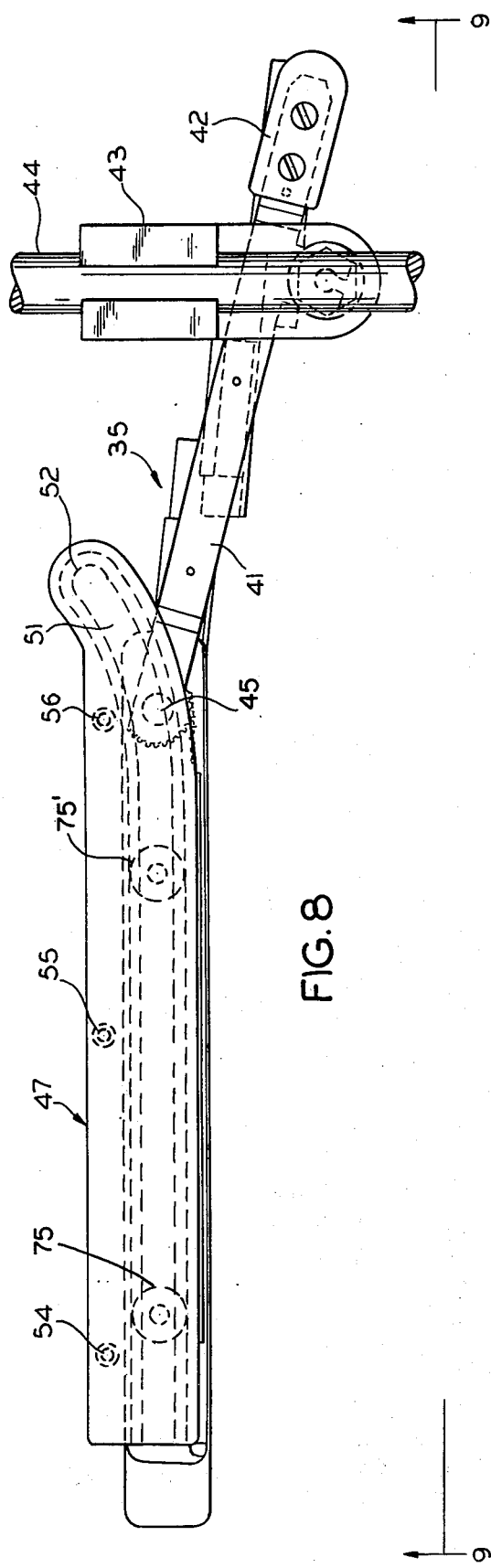
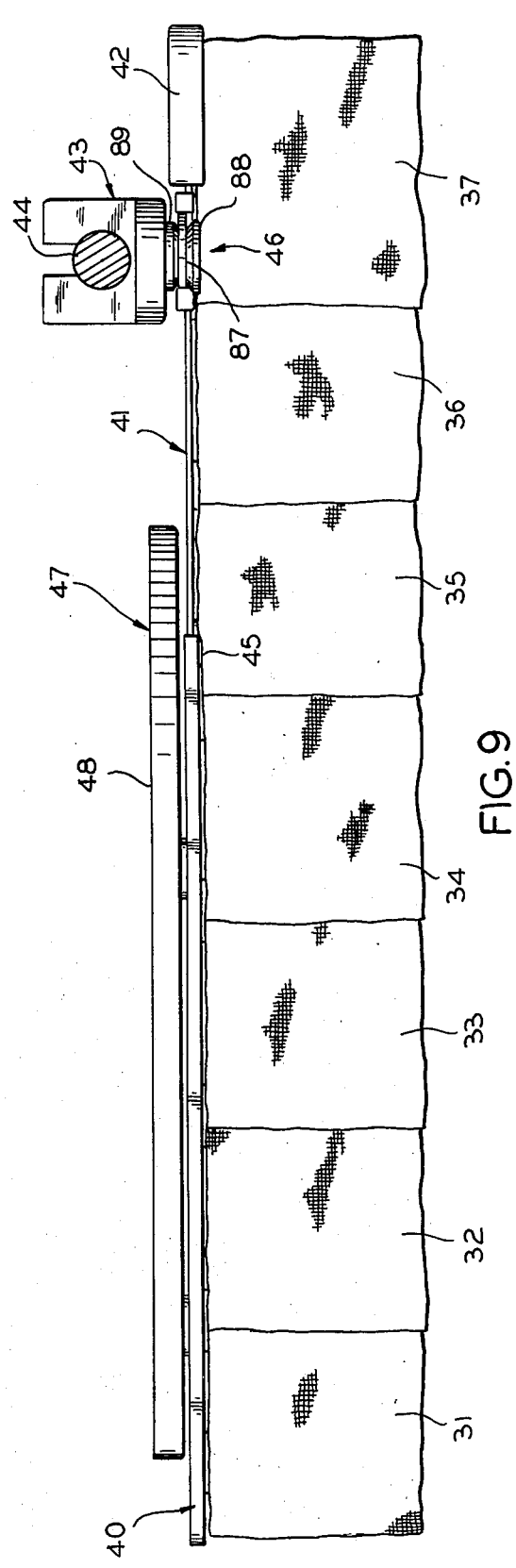
FIG. 8
FIG. 9

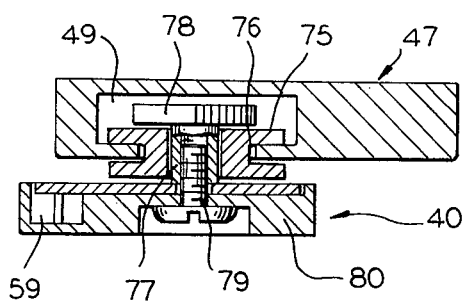
FIG.10
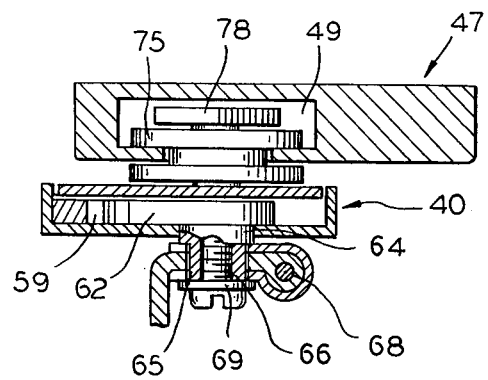
FIG.11
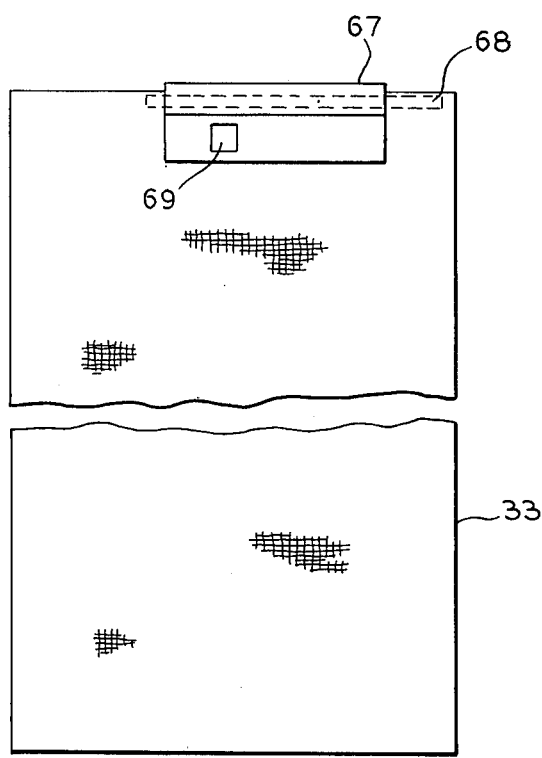
FIG.13
FIG.12

X-RAY SHIELDING DEVICE

BACKGROUND OF THE INVENTION

In diagnostic X-ray tables it is customary to suspend an X-ray absorbent curtain between a spot film device that extends over the table and the table top to shield a radiologist against radiation that is scattered from the patient and from parts of the table. The curtain is usually comprised of several flexible panels which may be spread apart to enable a radiologist to advance his hands towards the patient without interference. In some procedures, the X-ray table and the spot film device which it carries are jointly tilted to an upright position in which case it is desirable to have some of the panels disposed on the side of the spot film device to shield the radiologist in the position he must take next to the table top during the procedure.

Prior art x-ray protectives curtains were suspended from a single track mounted on a spot film device and had to be slid around to protect against scattered radiation emerging from the front and sides of the spot film device. In some apparatus, the front curtain panels spread apart at an improper angle for affording adequate protection during procedures which require the patient to be upright.

SUMMARY OF THE INVENTION

Among the objects of the present invention are to provide a mechanism which permits disposing first and second groups of flexible x-ray absorbent panels in shingled or overlapping relationship along the front of a spot film device such that the total length of the panels is greater than the width of the spot film device.

A further object and feature of the invention is that the second group of panels are mounted on a separate lever which may be actuated manually to dispose these panels along the side of the spot film device and to rotate the panels in the first group at the front to the best position for protecting against radiation that emerges toward the side and toward the gonadal area of the diagnostician when the table is positioned for an upright patient.

Another object of the invention is to provide means for automatically turning the curtain, or the apron as it is sometimes called, out of the way when the spot film device is pushed back to parked position transversely to the x-ray table top.

How the above and other more specific objects of the invention are achieved will appear in the course of and a description of, an illustrative embodiment of the invention which will be set forth hereafter in reference to the drawings.

A DESCRIPTION OF THE DRAWINGS

FIG. 4 is a plan view of the operating mechanism on which the panels are supported;

FIG. 5 is a plan view of a guide track as seen from the bottom, which receives the mechanism shown in the preceding figure;

FIG. 6 is an edge view of the track in FIG. 5;

FIG. 7 is an end view of the track looking in the direction of the arrows 7—7 in FIG. 6;

FIG. 8 is a top or plan view of the mechanism of FIG. 4 assembled into the track of FIG. 5, the mechanism being dismounted from the spot film device for the sake of clarity;

FIG. 9 is a front elevation view of the shielding device mechanism in FIG. 8 showing how the panels are disposed in a row to shield the front region of the spot film device;

FIGS. 10, 11 and 12 are sections taken respectively along the lines 10—10, 11—11, and 12—12 in FIG. 4; and FIG. 13 shows one of the x-ray shielding panels isolated from the curtain assembly.

DESCRIPTION OF A PREFERRED EMBODIMENT

Figure 1:
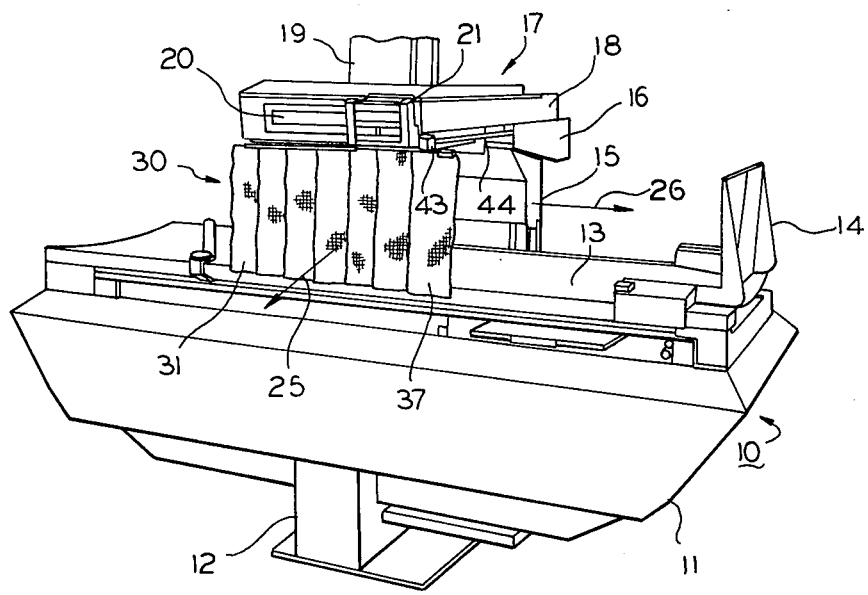
FIG. 1 shows a typical diagnostic x-ray table and combination fluoroscopic and spot film device which is provided with the new x-ray shielding device arranged for optimum shielding with the patient incumbent.

FIG. 1 shows a typical x-ray table 10 on which the new radiation shielding device may be used. The table comprises a body 11 which is mounted on a floor stand 12. The body 10 is adapted to tilt or angulate on a laterally directed axis in the counterclockwise direction and through a full 90° in the clockwise direction. The table has a longitudinally extending x-ray permeable top 13 on which a patient may be reposed for examination. At one end of the top there is a foot rest 14 for supporting the patient when the table is angulated to an upright position. Within the table body 11 there is an x-ray source, not visible, which projects a radiation beam upwardly through table top 13.

Mounted within the table body is a longitudinally movable carriage, not visible, that supports a vertically extensible and contractible column 15. At the top of column 15 there is a bearing support 16 for a combination fluoroscopic spot film device which is generally designated by the reference numeral 17. Spot film device 17 may be raised and lowered relative to table top 13 by extending or contracting column 15. Spot film device 17 may also be shifted laterally or crosswise of the table top 13 on bearing support 16. The spot film device is essentially conventional and comprises a housing 18 in which there is a mechanism, not visible, for advancing and retracting a film cassette in and out of the x-ray beam for enabling one or more x-ray exposures to be made on a single film. A fluoroscopic device 19 which may be an electronic x-ray image intensifier, shown fragmentarily, is mounted on top and near the front end of housing 18. The spot film device has a front door 20 for inserting and withdrawing a film cassette and it has an operating handle 21 which may be engaged manually to cause the spot film device to translate. All of the features of the x-ray table thus far described are conventional.

As is well known, when an x-ray beam is projected through a patient reposed on table top 13, some stray radiation is scattered by the body and by components of the x-ray table out of the space between spot film device 17 and table 13. To minimize the amount of scattered radiation that might reach an operator in the vicinity of x-ray table, a flexible x-ray shielding curtain or apron is customarily suspended from spot film device 17 toward table top 13. Scattered radiation having the general direction of the arrow 25 must be intercepted to protect an operator standing in front of the table when the table top is substantially horizontal and the curtain should be adapted for movement to the side of the spot film device to intercept radiation that might come from the side in the general direction of the arrow 26. When the table is tilted upright such as to erect the patient on foot rest 14 as is the case when vertical radiography or fluoroscopy is to be performed, the radiologist may be sitting or standing in a position facing the table top in which case he may be in the path of scattered radiation that may emerge generally perpendicular to the arrow 26. Thus, the x-ray protective apron should have the capability of intercepting scattered radiation regardless of the location of the attending radiologist and regardless of the angular attitude of the table and spot film device.

Referring to FIG. 1, the new x-ray shielding device uses several flexible x-ray absorbent curtain panels which are designated collectively by the reference numaeral 30. These panels may be made of polyvinyl that is impregnated with lead. As shown in FIG. 1, the panels between the first panel 31 and the last panel 37 are in a substantially straight row and are suspended in overlapping relationship similar to shingles to close the spaces between them. As can be seen, the total width of the panels 31-37 is greater than the width of the spot film device and when they are arranged in a substantially straight line across the front of the spot film device as they are shown, they afford a maximum protection to the radiologist standing in front of the x-ray table and spot film device. The panels may also be arranged at the side of the spot film device while still affording protection against radiation that emerges from the front. The construction and operation of the new mechanism for supporting and positioning the panels will now be described in greater detail.

The general features of the new curtain support mechanism will be outlined first in reference to FIGS. 8 and 9. In FIG. 9, the flexible panels 31-37 are shown arranged in a straight line as they are in FIG. 1. In this example, four of the panels 31-34 comprising a first group, are supported from a mechanism in an elongated carrier means 40 which contains a mechanism for rotating panels 31-34 about a central vertical axis incidental to disposing the other three panels 35-37, comprising a second group, along the side of the spot film device. Panels 35-37 are supported on elongated means such as a lever 41 that terminates in a manually engageable handle 42. Lever 41 is pivotally connected to elongated housing 40 with a pin 45. Lever 41 may be selectively coupled and uncoupled with respect to a laterally movable guide block 43 that serves as a linear bearing for sliding on a rod 44 that is mounted on a side of the spot film device and directed laterally or, in other words, crosswise of the x-ray table. Since lever 41 is pivotal on pin 45 with respect to elongated carrier means 40, if the lever is pushed away from the observer in FIG. 9 three panels 35-37 comprising the second group will be disposed in a substantially coplanar fashion along the side of the spot film device while the other panel 31-34 comprising the first group will be rotated to present their faces in the same direction as panels 35-37. Lever 41 is selectively coupled and uncoupled to bearing block 43 with a coupling device that is generally designated by the reference number 46 in FIG. 9. Mechanism housing, or carrier, 40 is supported in a guide or track 47. Track 47 is mounted to the bottom of the spot film device housing near the front thereof. The top surface 48 of track 47 interfaces with the bottom surface of the spot film device housing 18.

FIGS. 5-7 show the details of track 47. The track has a T-shaped slot 49 which has a straight portion 50 and a curved portion 51 and a closed end 52. End 53 of the track is open. Several holes 54-56 are provided for fastening the track to the bottom of the spot film housing with screws. not shown. FIG. 5 is a bottom view of track 47 which would be inverted when mounted to the spot film device and would appear from the top as in FIG. 8.

The means for actuating or rotating panels 31-34 in the first group in response to lever 41 being pivoted will now be discussed. Referring to FIG. 4, one may see that lever 41 is mounted for pivoting on a shaft 45 that is carried by the elongated carrier 40. Lever 41 has a gear sector 58 formed at its end. The gear sector teeth engage with a slideable toothed rack 59 which is slideable lengthwise of elongated carrier means. Rack 59 is engaged by four gear sectors 60-63 such that when the rack is translated the gear sectors will rotate. In this design, the sectors can rotate approximately 90°. A typical gear sector 62 may be seen in FIG. 11. It has a shaft fastened to it. The shaft comprises a cylindrical bearing portion 64 and another portion 65 which is square in cross section. The shaft has a bore for receiving a screw 66 that serves to attach the shaft to gear sector 62. The square section 65 of the shaft extends from the bottom of guide housing 40 and provides a means for mounting a flexible x-ray shielding panel such as the one marked 33 in FIG. 13. This figure shows a panel as it appears before it is mounted to the shaft extending from gear sector 62. The panel 33 may be a double layer of polyvinyl that is sealed at its margins and contains a lead impregnated sheet of flexible plastic material, not shown.

The flexible panel has a clip 67 at its top for stiffening the top margin of the panels. The clip may be metal or plastic material. Within the top margin of the panel is a rod 68 which provides additional stiffening where required. The panel and clip are provided with a square hole 69. The square hole enables the panel to be slid onto the square portion 65 of the shaft in FIG. 12 and to be held in place by the screw head and washer 69. It will be evident that when gear sector 62 rotates, the square shaft will cause panel 33 to rotate through a corresponding angle. The other panels 31, 32 and 34 in the first group are similarily mounted for rotation with gear sectors 60, 61 and 63, respectively.

The carrier or housing 40 is adapted to be engaged with track 47 which is fixed to the bottom of the spot device. The carrier is capable of sliding in parallelism with the track 47 as required during operation of the curtain mechanism and it is also completely removable from the track when storage of the curtain assembly away from the x-ray table is desired.

As shown in FIG. 4, at the top of carrier 40 there are a pair of rollers or wheels 75 and 75 which, as can be seen in FIG. 10, have a groove 76 in their peripheries for engaging with the shoulders of the T-shaped slot 49 in track 47. The typical grooved wheel 75, shown in FIG. 10, turns on a bushing 77 which has a head 78. The bushing has an internally threaded bore which receives a screw 79 which mounts the bushing to a block 80 within the elongated carrier 40. Because of the open end 53 in the T-shaped slot 49, wheels 75 and 75 and carrier 40 on which they journaled may be slid in and out of the track 47 and required.

Lever 41, as shown in FIGS. 4 and 8, has the second group of three panels 35, 36 and 37 attached to it. The panels are disposed in overlapping relationship along the length of handle 41 and, in this embodiment, do not rotate thereon. FIG. 12 shows how one of the panels 36 is secured to lever 41 with a screw 81 that passes through a clip 82 which is similar to clip 67 in FIG. 13 except that it does not have a square hole. The three panels 35-37 remain essentially in the same vertical plane as handle 41.

Lever 41 in FIG. 4 is provided with an extension 85 near handle 42. Extension 85 has a key slot 86 for engaging it with a cylindrical spring biased detent 87 which has a beveled head 88. The beveled surface of head 88 is in complementary spaced relationship with stationary beveled nut head 89. Thus, lever 41 may be rapidly attached or detached from detent shaft 87 by engaging and disengaging key slot 86 with respect to the detent. When it is attached, rotation of lever 41 causes bearing block 43 to slide on rod 44 whereupon panels 35, 36 and 37 are disposed along the side of the spot film device. It will be evident in FIG. 8 that when bearing block 43 has been advanced sufficiently toward the rear of the spot film device, leading grooved roller on wheel 75 will begin to follow the curved portion 51 of track 47 and will ultimately stop against the end 52 of the track.

Figure 2:
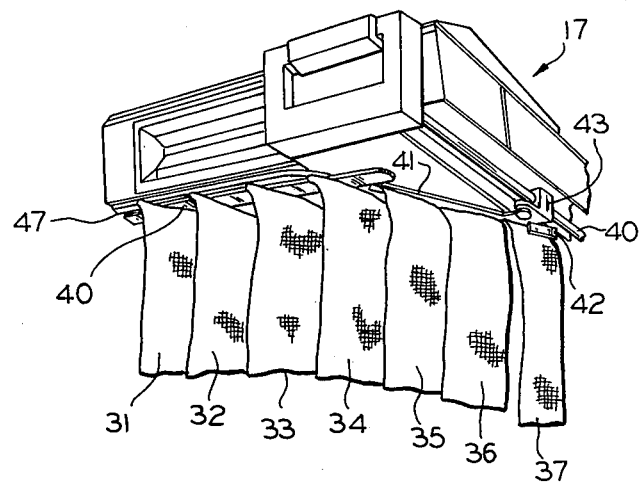
FIG. 2 shows a portion of the spot film device broken away and enlarged to illustrate how the mechanism is arranged when the shielding panels are disposed in the front and at the side of the spot film device, but is should be understood that the mechanism would normally be in this position when the x-ray table it tilted as shown in FIG. 3.

FIG. 2 is presented solely for the purpose of showing how the elongated carrier 40 and lever 41 are related when panels 31-34 are at the front and panels 35-37 are at the side of spot film device 17. Normally the panels would be at the front and side when the x-ray table and spot film device are tilted as in FIG. 3 but, in this figure, the panels conceal the carrier and lever mechanism. When the diagnostician works with the patient and table horizontal as in FIG. 1, he will have the panels 31-37 arranged in a line across the front of the spot film device as shown in that figure. In accordance with the invention, when the table is tilted, the carrier 40 and lever 41 will automatically assume the position in which they are shown in FIG. 2 but, more realistically, the panels 31-37 will hang down as shown in FIG. 3.

Refer to FIGS. 8 and 9 for a further description of the automatic panel shift feature. As shown, the handle 41 is angulated slightly so it is not in line with the track 47. Since sliding bearing 43 is constrained against moving closer to the observer as depicted in FIG. 8, a toggling effect is produced, which means that if the table and spot film were to be tilted, the track and lever would remain in a slightly angular relationship or in substantially a straight line as in FIG. 8.

Figure 3:
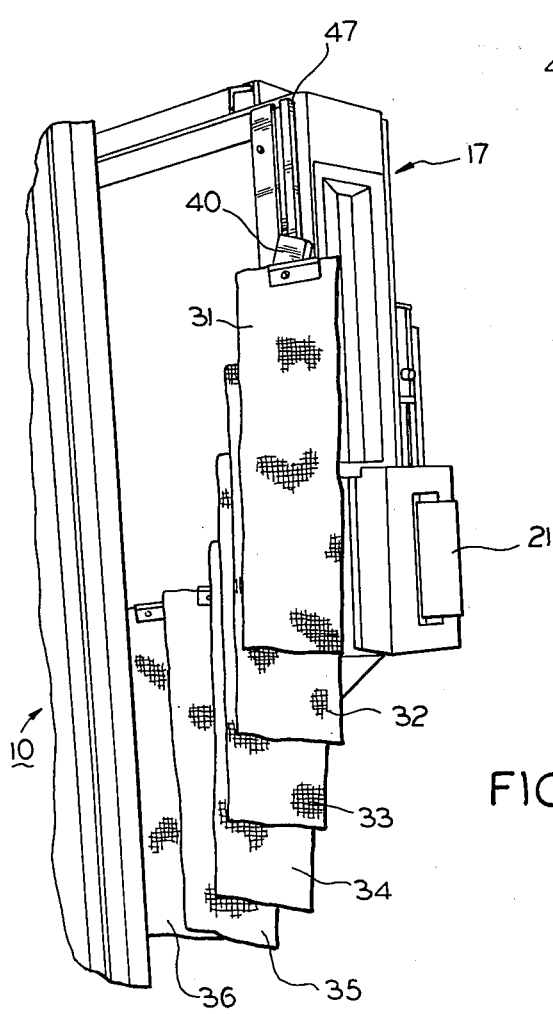
FIG. 3 shows how the panels hang when the framentarily shown x-ray table and spot film device are angulated to a vertical position.

If, however, the sliding bearing 43 and lever 41 are set slightly ahead of track 47 or in line with it, the panels 31-37 would be in substantially a straight line but, if the table were tilted, the handle 41 would swing automatically around to the side of the spot film device to dispose the panels as shown in FIG. 3. Automatic action results from track 47 having a curved end portion 51 as can be seen in FIG. 8. When the table is tilted, and if the handle 41 is not toggled toward the observer as in FIG. 8, the weight of the panels and their carrier 41 will cause the leading roller 75 on the carrier to enter or roll into curved portion 51 of the track, thus causing lever 41 to swing and causing bearing block 43 to advance along rod 43. This results in the x-ray absorbing panels becoming arranged automatically, as in FIG. 3, when the x-ray table and spot film device are angulated.

A feature of the invention is that when the panels are disposed as in FIG. 2 or 3, for instance, simply pushing the spot film device 17 rearwardly on its bearing support 16 to park it rearward of the table results in bearing block 43 stopping against support 16 which deflects lever 41 and places all of the panels 31-37 in alignment with each other in a neat arrangement at the rear of the table top and clear of it.

In FIG. 3, table 10 and spot film device 17 are angulated clockwise from the position in which they appear in FIG. 1 such as is the case when the radiologist desires to perform fluoroscopy with the patient in an upright position and standing on foot rest 14. During this procedure, the radiologist will usually be positioned adjacent the top of the spot film device in which case stray radiation that would tend to pass the front of the spot film device is intercepted by the rotated panels 31-34 and radiation emanating along the length of the spot film device is intercepted by the combined action of panels 31-34 and panels 34-37.

The x-ray shielding pattern thus formed by the panels will intercept scattered radiation directed toward the gonadal region of the diagnostician when he or she is position adjacent an upright x-ray table for viewing an image intensifier output mirror or a television monitor in customary fashion.

Although a preferred embodiment of the new curtain assembly has been described in considerable detail, such description is intended to be illustrative rather than limiting, for the invention may be variously embodied and is to be limited only by interpreting the claims which follow.

We claim:

1. An x-ray shielding device for use with an x-ray table having a top for supporting an examination subject and having x-ray imaging apparatus extending over said top and in spaced relationship therewith, said shielding device comprising:
   first elongated means for being disposed substantially between said table top and said imaging apparatus,
   a first group of x-ray shielding panels and rotatable means respectively supporting said panels from said first elongated means for rotation about the respective axes of the panels,
   a second elongated means pivotally connected to said first elongated means for being disposed alternately substantially in line with said first elongated means and at angles relative to it,
   a second group of x-ray shielding panels mounted to said second elongated means, and
   means responsive to pivoting of said second elongated means by rotating said rotatable means and the said first group of panels.

2. The device as in claim 1 including:
   means for supporting said first elongated means for limited translation generally lengthwise of said table top,
   guide means extending substantially crosswise of said table top and mounted to said imaging apparatus,
   bearing means that are translatable along said guide means, and
   means for selectively engaging said second elongated means with said translatable bearing means.

3. The device as in claim 2 wherein:

said second group of shielding panels are generally rectangular and have their widths extending generally along said pivotal second elongated means.

4. The device as in claim 2 wherein said means for supporting said first elongated means comprises:
guide track means for being mounted to said imaging apparatus and having a straight track portion and a curved track portion that curves generally in the crosswise direction of said top,
roller means mounted in spaced relationship on said first elongated means and engageable with said guide track means.

5. The device as in claim 1 including:
a plurality of gear means journaled for rotation on said first elongated means and coupled respectively with said panels in said first group,
a tooth gear rack translatable on said first elongated means and engaged with said gear means, respectively,
a driving gear that is rotatable in response to pivoting said second elongated means and is engaged with said gear rack for translating the same and rotating said plurality of gear means and panels simultaneously.

6. An x-ray shielding device for use with a tiltable x-ray table having a longitudinally extending table top and x-ray imaging apparatus extending laterally of the top in spaced relationship therewith and having a longitudinally disposed front end and a laterally disposed side, said device comprising:
groups of flexible x-ray shielding panels for being disposed selectively along the front and sides of said apparatus,
guide track means for being mounted at the front of said apparatus and extending generally longitudinally,
support means and means for engaging said support means with said guide track means for said support means to translate thereon,
a plurality of rotatable means which are mounted for rotation on said support means and which respectively support the panels in one group,
lever means pivotally connected with said support means, and panels in another group being disposed along said lever means and suspended therefrom, and
driving means responding to pivoting of said lever means by rotating said rotatable means.

7. The device as in claim 6 wherein:
said support means comprises an elongated means and said rotatable means are rotatable from a first angular position wherein the panels in said one group extend in overlapping substantially coplanar relation across the front of said imaging apparatus to a second angular position wherein said panels are in substantially parallel spaced apart planes,
said panels of said other group being arranged on said lever means to be substantially coplanar with the panels in said one group when said rotatable means are in said first angular position and to be closer to perpendicularity with the panels in said one group when said rotatable means are in said second angular position.

8. The device as in claims 6 wherein:
said driving means comprises gear means operatively connected to said rotatable means, respectively,
a rack translatable on said support means and having teeth engaged with each of said gear means,
another gear means rotatable in response to rotation of said lever means and engaged with said rack for translating it.

9. The device as in claim 6 including:
rod means disposed generally laterally at the side of said imaging apparatus,
a member that is translatable on said rod means, and
means for selectively and pivotally engaging said lever means with said translatable member.

10. The device as in claim 9 wherein:
said means for engaging said support means with said guide track means comprise roller means journaled for rotation on said support means,
said guide track means having a slot for said roller means to translate along, said slot having a straight portion and a continuous portion curved away from said front for said roller means to enter when said lever means is pivoted substantially laterally.

11. An x-ray shielding device for use with a tiltable x-ray table which has a top for supporting an examination subject and x-ray imaging apparatus extending crosswise over said top and in spaced relationship therewith, said shielding device comprising:
first guide means mounted to said imaging apparatus and extending generally lengthwise of said table top,
carrier means translatable on said guide means,
a first group of x-ray shielding panels mounted to said carrier means,
lever means pivotally connected with said carrier means,
a second group of x-ray shielding panels mounted to said lever means,
second guide means mounted to said imaging apparatus and extending generally crosswise of said table top,
means that are translatable along said second guide means and means for alternately connecting and disconnecting said lever means to said translatable means,
tilting of said table from a substantially horizontal position causing said carrier means to translate on said first guide means under the influence of gravity and, when said lever is connected, to pivot said lever means for translation on said second guide means for rearranging said panels relative to said apparatus.

12. The shielding device as in claim 11 including:
means supporting the respective panels in said first group for rotation on said carrier means, and
means responsive to pivoting of said lever means by rotating said panels in said first group.

13. The device as in claim 12 wherein:
said first guide means is an elongated track having a curved portion near its end, and
roller means engaging said carrier means with said track for said translation, said roller means entering said curved track portion when said table is being tilted to influence pivoting of said lever means.

* * * * *